United States Patent
Sheldon et al.

(10) Patent No.: US 6,449,508 B1
(45) Date of Patent: Sep. 10, 2002

(54) ACCELEROMETER COUNT CALCULATION FOR ACTIVITY SIGNAL FOR AN IMPLANTABLE MEDICAL DEVICE

(75) Inventors: Todd J. Sheldon, Eagan; Donald Ruzin, Roseville, both of MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/422,835

(22) Filed: Oct. 21, 1999

(51) Int. Cl.[7] .............................................. A61N 1/365
(52) U.S. Cl. ......................................... 607/19; 600/595
(58) Field of Search ............................... 600/587, 595, 600/509; 607/9, 17–19; 128/902

(56) References Cited

U.S. PATENT DOCUMENTS

| | | | |
|---|---|---|---|
| 4,374,382 A | 2/1983 | Markowitz | 340/870.01 |
| 4,476,868 A | 10/1984 | Thompson | 128/419 PG |
| 4,485,813 A | 12/1984 | Anderson | 128/675 |
| 4,556,063 A | 12/1985 | Thompson | 128/419 PT |
| 4,940,053 A | 7/1990 | Mann | 128/419 PG |
| 5,031,614 A | 7/1991 | Alt | 128/419 OPG |
| 5,040,535 A | 8/1991 | Mann | 128/419 PG |
| 5,052,388 A | 10/1991 | Sivula | 128/419 PG |
| 5,127,404 A | 7/1992 | Wyborny | 128/419 P |
| 5,179,974 A | 1/1993 | Taniguchi | 137/554 |
| 5,215,084 A | 6/1993 | Schaldach | 128/419 PG |
| 5,243,979 A | * 9/1993 | Stein et al. | 607/20 |
| 5,562,711 A | * 10/1996 | Yerich | 607/17 |
| 5,635,640 A | 6/1997 | Geen | 73/504.12 |
| 5,649,968 A | 7/1997 | Alt | 607/19 |
| 5,674,258 A | 10/1997 | Henschel | 607/19 |
| 5,885,471 A | 3/1999 | Ruben | 216/33 |

* cited by examiner

*Primary Examiner*—Kennedy Schaetzle
*Assistant Examiner*—Kristen Drosech
(74) *Attorney, Agent, or Firm*—Girma Wolde-Michael

(57) ABSTRACT

Different levels of accelerometer output are monitored separately and the outputs from these separate monitorings are combined with weighted values to produce a more responsive accelerometer output or count signal. The value of the weights varies with the level monitored. The method and apparatus can be used independently or combined with other cardiac demand signals to produce a pacing rate or target pacing rate signal or can provide data for monitoring, research, or therapeutic intervention.

8 Claims, 7 Drawing Sheets

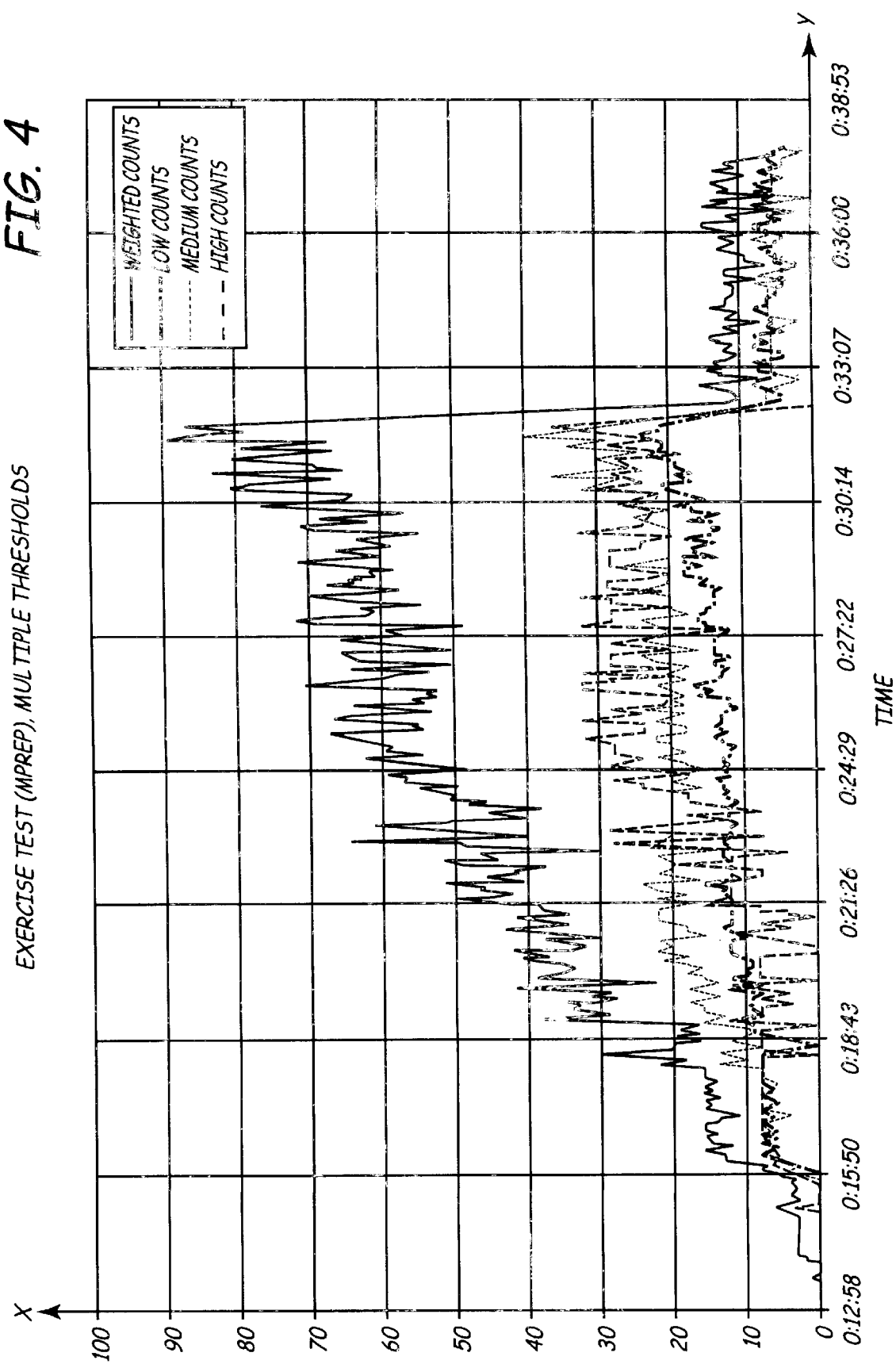

ACCELEROMETER COUNT CALCULATION FOR ACTIVITY SIGNAL FOR AN IMPLANTABLE MEDICAL DEVICE

FIELD OF THE INVENTION

This invention relates to determination of activity levels for living beings wearing or having implantable medical devices and particularly to how to determine appropriate values for such activity levels using accelerometer output signal.

BACKGROUND OF THE INVENTION

A wide assortment of body-implantable medical devices may employ activity level signals for a) maintaining records of patient activity, or for b) providing input to devices that deliver therapy. For example, a cardiac pacemaker can adjust a pacing rate in response to higher levels of indicated patient activity, assuming that cardiac demand will respond to the activity and that increasing the pacing rate will fulfill that demand better. Activity levels can be useful for diagnostic purposes too, and having a record of patient activity can provide a window into the state of that patient's state of health.

Examples of activity sensors from the prior art are described in, The following U.S. Patents; Schaldach U.S. Pat. No. 5,215,084, Alt, et al., U.S. Pat. No. 5,649,968, Mann et al., U.S. Pat. Nos. 5,040,535 and 4,940,053, Meyerson et al., U.S. Pat. No. 5,179,974, and Alt, U.S. Pat. No. 5,031,614, all incorporated herein by this reference in their entireties.

Each type of activity signal in the art has strengths and weaknesses relative to accuracy in tracking cardiac demand. Much development work has gone into multisensor systems of which the U.S. Pat. No. 5,562,711 to Yerich, is an example. This patent is also incorporated herein by this reference in its entirety.

There is certainly a need for more refinement in the activity signals available and how to best process them, especially as the art moves from piezocrystal activity crystal sensors to accelerometers.

SUMMARY OF THE INVENTION

Generally we take a plurality of thresholds and apply them to what amount to or may be copies of the accelerometer output signal. From these we get a plurality of different activity counts from the same accelerometer output signal. We then weight them according to a sensitivity setting and combine the count values to establish the preferred count value. We can store this value for recording the patient activity level or use it for diagnostic purposes, or for therapy alteration purposes as in, changing the pacing rate, for example.

We cyclically change the accelerometer circuitry's sensitivity for each short period (we prefer two second periods) to one of (preferably) three settings that are based on the programmed activity threshold. The activity counts obtained at each sensitivity setting will be weighted such that activity counts obtained at less sensitive levels will be more heavily weighted. These activity counts are then combined to create a sensor count value. This value is used to determine the Target Rate. If the current pacing rate, called the Sensor Rate is above (below) the Target Rate, the Sensor Rate will decelerate (accelerate) towards the Target Rate. The acceleration and deceleration of the Sensor Rate towards the target rate is represented by the smoothing of the acceleration/deceleration shown in block 47 of FIG. 3.

BRIEF DESCRIPTION OF THE DRAWINGS

The foregoing and other aspects and features of the present invention can be better appreciated with reference to a detailed description of a specific embodiment of the invention, when read in conjunction with the accompanying drawings, wherein:

FIG. 4 is a four line graph showing the High, Medium and Low counts from thresholded signals from accelerometer sensor output, and the tallest curve is the Weighted Counts curve, in accord with an embodiment of the invention;

DETAILED DESCRIPTION OF A SPECIFIC EMBODIMENT OF THE INVENTION

GENERAL DESCRIPTION

It should be noted that the invention herein may be used with implantable or wearable devices of any kind if it is valuable to know what kind of activity a patient or person wearing or implanted with such a device is undertaking. Activity sensing has demonstrated particular value for pacemakers and implantable monitors for monitoring heart function. Although the invention's application is not limited to such devices, a pacemaker is used to illustrate the invention herein.

Figure 1:
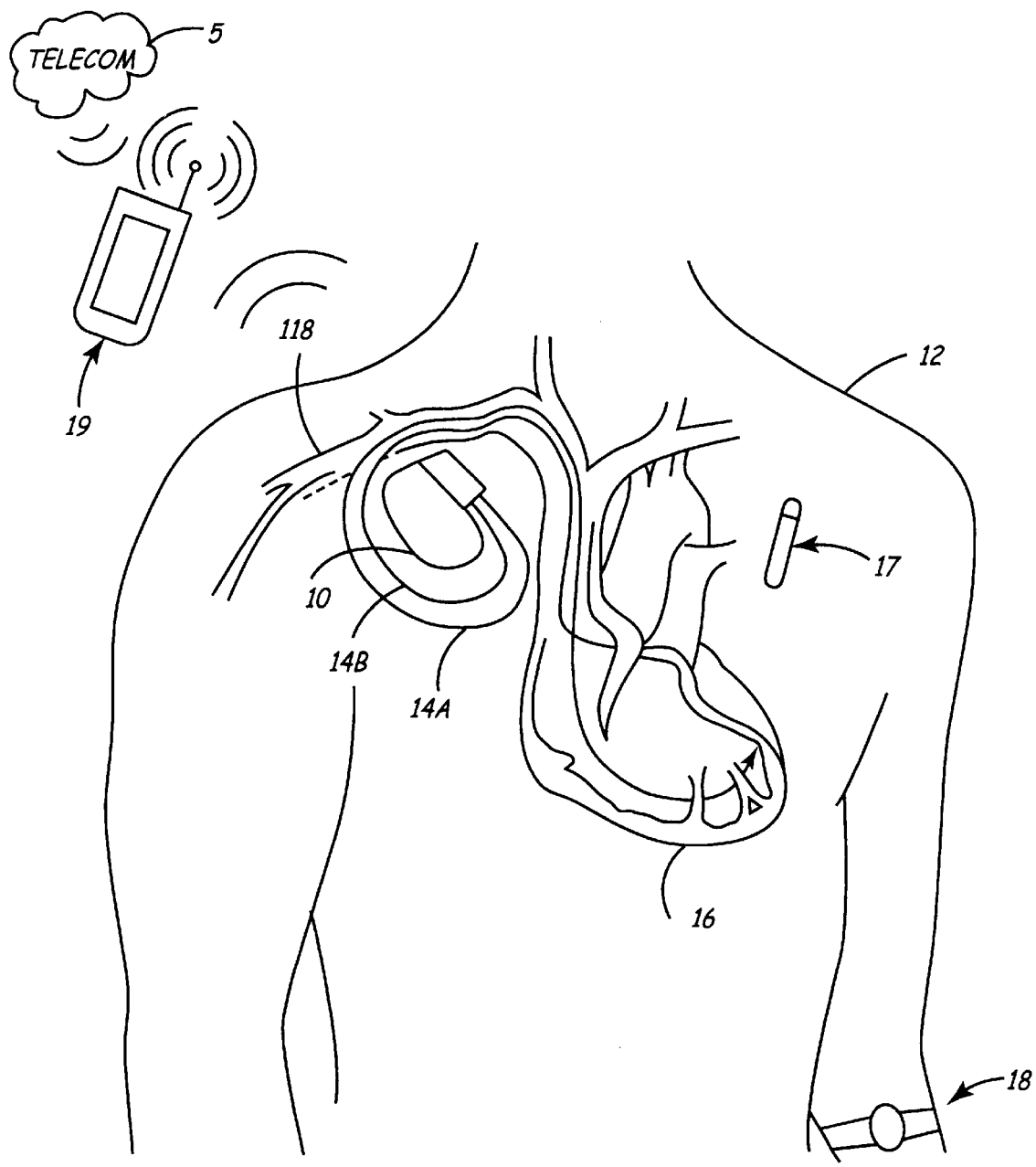
FIG. 1 is an illustration of devices, which can employ this invention including a pacemaker and another medical device having been implanted into a human patient, a wearable device that could employ the invention and communications equipment for use with the invention.

Referring to FIG. 1, a pacemaker 10, being an exemplary device for use of this invention, in accordance with one embodiment of the invention may be implanted in a patient 12. In accordance with conventional practice in the art, pacemaker 10 is housed within a hermetically sealed, biologically inert outer canister, which may itself be conductive and thus serve as an indifferent electrode in the pacemaker's pacing/sensing circuit. One or more pacemaker leads, collectively identified with reference numerals 14a (ventricular) and 14b (atrial) in FIG. 1 are electrically coupled to pacemaker 10 in a conventional manner, extending into the patient's heart 16 via a vein 18. Disposed generally near the distal end of leads 14a and 14b are one or more exposed conductive electrodes for receiving electrical cardiac signals and/or for delivering electrical pacing stimuli to heart 16.

Alternative devices which may be used are illustrated for example purposes only, including the implantable monitoring device 17 and a wrist worn monitoring device 18, but clearly any device where the invention could be applied should not be excluded from use as a system into which the inventive features may play a role. Whatever the embodiment, it is useful, although not imperative, to be able to communicate the data from within the device (which may have been gathered in reliance on the invention or through other means) to devices which can be used to display the data in various raw or refined forms, and which may communicate back instructions to alter the programming of the implantable or wearable device(s). Thus in FIG. 1, there is illustrated an external programmer device 19, which may telemetrically communicate with the example devices 10, 17 and/or 18 for these or other purposes. The communication can of course be made even more useful by enabling the programmer 19 to link to a telecommunications network 5, through which a health care professional can review the communications and the data and respond appropriately, or through which records or research can be automatically retained and organized by computing systems (not shown) connected to the telecommunications network 5.

To the extent that certain components of pacemaker 10 are purely conventional in their design and operation, such components will not be described herein in detail, as it is believed that design and implementation of such components would be a matter of routine to those of ordinary skill in the art and will vary considerably where the invention is used inside other devices. For examples of common component systems, consider a known pacing/control circuit which includes sense amplifier circuitry, pacing output circuitry, a crystal clock, a random-access memory and read-only memory (RAM/ROM) unit, a central processing unit (CPU), and a telemetry circuit. Even components like an accelerometer itself can be found in common devices.

Figure 2:
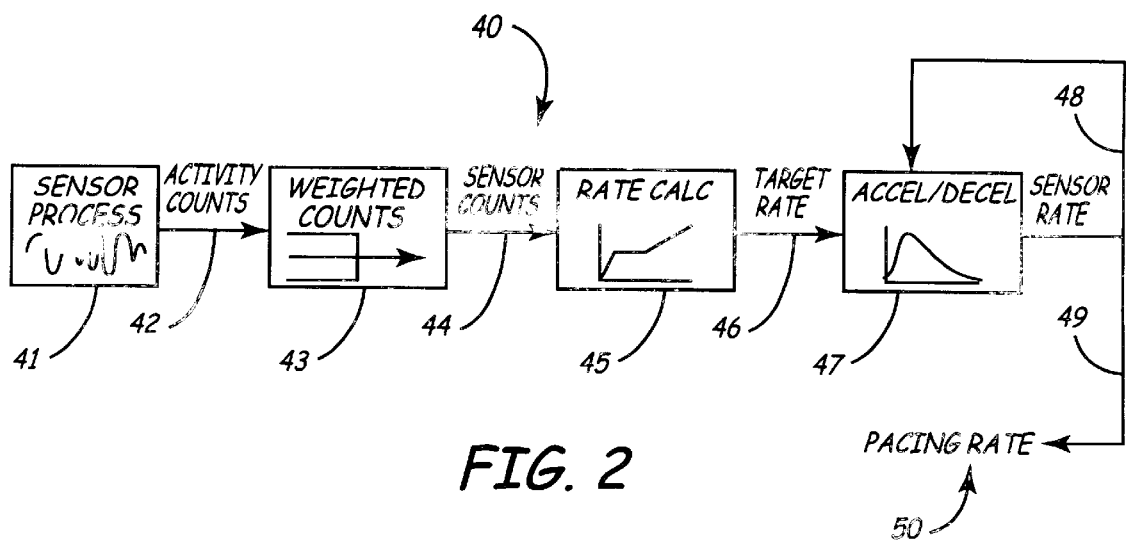
FIG. 2 is a block diagram of the sensor rate processing in accord with an embodiment of the invention.

Turning now to FIG. 2, there is shown a block diagram of the electronic circuitry that makes up pacemaker 10. In this embodiment, we illustrate what should be thought of as a secondary cardiac demand measuring system for the purposes of this invention, since this invention relates to use of an accelerometer by itself primarily, but the use of an additional cardiac demand parameter measuring sensor should be considered as available for use with this invention. Such an additional sensor can be used in order to complement the limitations of accelerometer signals in accurately measuring or identifying a level of cardiac demand.

As can be seen from FIG. 2, pacemaker 10 comprises a primary pacing/control circuit 20, an activity sensor circuit 21, which will produce the activity signal used in this invention, and a minute ventilation circuit 22, which produces a signal also related to cardiac demand. Much of the circuitry associated with pacing control circuit 20 can be of conventional design, in accordance, for example, with what is disclosed in U.S. Pat. No. 5,052,388 to Sivula et al, entitled "Method and Apparatus for Implementing Activity Sensing in a Pulse Generator." The Sivula et al. '388 patent is hereby incorporated by reference herein in its entirety. To the extent that certain components of pacemaker 10 are purely conventional in their design and operation, such components will not be described herein in detail, as it is believed that design and implementation of such components would be a matter of routine to those of ordinary skill in the art and will vary considerably where the invention is used inside other devices. For examples of common component systems consider the pacing control circuit 20 in FIG. 2 which includes sense amplifier circuitry 24, pacing output circuitry 26, a crystal clock 28, a random-access memory and read-only memory (RAM/ROM) unit 25, a central processing unit (CPU) 23, and a telemetry circuit 27. Even components like the accelerometer 29 itself can be found in common devices.

The telemetry circuit of the preferred exemplary embodiment, has an antenna, so that it is capable of being programmed by means of external programmer/control unit 19 (shown in FIG. 1). Alternate means for programming and communication are known and may be used, of course, since the invention centers on the accelerometer output signal and its conversion into useful data.

Known programmers typically communicate with an implanted device via a bidirectional radio-frequency telemetry link, so that the programmer can transmit control commands and operational parameter values to be received by the implanted device, and so that the implanted device can communicate diagnostic and operational data to the programmer. Activity data and data related to it would likely be considered diagnostic data. Example programmers suitable for the purposes of practicing the present invention are the Model 9760 and Model 9790 Programmers, available from Medtronic, Inc., Minneapolis, Minn. Some examples of current telemetry systems believed to be suitable for the purposes of practicing the present invention are disclosed in the following U.S. Patents: U.S. Pat. No. 5,127,404 to Wyborny et al. entitled "Telemetry Format for Implanted Medical Device"; U.S. Pat. No. 4,374,382 to Markowitz entitled "Marker Channel Telemetry System for a Medical Device"; and U.S. Pat. No. 4,556,063 to Thompson et al. entitled "Telemetry System for a Medical Device". The Wyborny et al. '404, Markowitz '382, and Thompson et al. '063 patents are commonly assigned to the assignee of the present invention, and all are hereby incorporated by reference herein in their respective entireties.

As previously noted, the known pace/control circuit includes a central processing unit which may be an off-the-shelf programmable microprocessor or microcontroller, but in the presently preferred embodiment of the invention is a custom integrated circuit. It will be apparent to those of ordinary skill in the art that the central processing unit of the pace/control circuit functions to control the timed operation of the pacing output circuit and the sense amplifier circuit under control of programming stored in the RAM/ROM unit. Those of ordinary skill in the art will be familiar with such an operative arrangement.

A crystal oscillator circuit of the known pace/control circuit provides main timing clock signals for coordinating the operation of the circuitry.

It is to be understood that the various components of pacemaker 10 depicted in FIG. 1 may be powered by means of a battery (not shown), which is contained within the hermetic enclosure of pacemaker 10, or they may be powered by any other power source, in accordance with practice in the art.

The pacing output circuit, which function to generate pacing stimuli under control of signals issued by the CPU, may be, for example, of the type disclosed in U.S. Pat. No. 4,476,868 to Thompson, entitled "Body Stimulator Output Circuit," which patent is hereby incorporated by reference herein in its entirely.

The pace/control circuit is coupled to the activity sensor circuit and a minute ventilation circuit by means of multiple signal lines, designated collectively as BUS. A set of I/O interface coordinate the transmission of signal through the BUS. Alternative arrangements for data communication are acceptable so long as they do not impair the operation of the invention. communication are acceptable so long as they do not impair the operation of the invention.

ACTIVITY SENSING

As previously noted, the example embodiment pacemaker 10 in accordance with one preferred embodiment of the invention may use both activity sensing and minute ventilation measurement in establishing a variable rate-responsive pacing rate.

In the preferred embodiments, the activity sensor circuit in pacemaker 10 utilizes an accelerometer as a sensor for activity sensing. Such an accelerometer is in our preferred embodiments mounted directly to the hybrid or circuit board in our implantable medical devices. It is designated with reference numerals 29a and 29b in FIGS. 10 and 11, respectively. In the prior art, a piezo-crystal sensor was bonded to the inner surface of the pacemaker's hermetic enclosure, in accordance with conventional practice in the art, or otherwise connected to the circuitry in any stable location in the device. Such an arrangement is disclosed, for example, in the above-referenced U.S. Pat. No. 4,485,813 to Anderson et al., assigned to the assignee of the present invention and hereby incorporated by reference herein in its entirety. A similar arrangement is also disclosed in the above-referenced U.S. Pat. No. 5,052,388 to Sivula et al. The sensor may be constructed in accord with any accelerometer having an appropriate signal output range for acceleration in the range of approximately 0 (zero) to about 1 g that can be measured by appropriate or conventional circuitry. It is possible to use a sensor that has a piezo electric, a capacitive or even an optical pickoff for producing the relevant acceleration signal. While such a piezo sensor could be used, the economics of adopting a sensor that is easily bonded on to or formed on the hybrid circuit board makes it much less preferred.

In the current embodiments we employ an accelerometer similar to what is described in U.S. Pat. Nos. 5,885,471 and 5,674,258, incorporated herein by this reference, and we use a piezoelectric pickoff for generating the accelerometer signal. However, multi-finger capacitive pickoff accelerometers such as are illustrated for example in U.S. Pat. No. 5,635,640 could also be used. Piezoelectric or capacitive pickoff of the accelerometer signal can be used as preferred for the particular embodiment selected by the designer, and in fact, one could even use the prior art activity crystals in less preferred embodiments if desired. The base requirement is that the accelerometer signal produce a repeatable amplitude varying output signal that increases with greater acceleration, or at least varies directly with acceleration, and the range of acceleration measured is suitable for the task of measuring an individual's activity levels.

An activity sensor provides a raw electrical signal to an activity signal processing circuit ACT PROC in the activity circuit, which bandpass filters and processes the activity signal for use in establishing the pacemaker rate. Peaks in the bandpass-filtered activity signal that exceed series of predetermined thresholds are interpreted by the activity signal processing circuit as an indication of patient activity. These thresholds in the preferred embodiment are selectively programmable and intended to screen out background "noise" in the sensor output signal indicative of low patient activity, or of physical stresses detected by the activity sensor which are not actually indicative of patient activity.

(The concept of deriving, activity "counts" representative of the level of a patient's physical activity, is well known and understood in the prior art, as exemplified by the above-noted Anderson '813 and Sivula '388 patents, and will thus not be described herein in additional detail. It is believed that those of ordinary skill in the art will be familiar with utilization of a piezoelectric sensor to perform activity sensing in an activity-responsive cardiac pacing and will be readily able to implement such a capability in a manner suitable for the purposes of practicing the present invention.)

In FIG. 2, the sensor process signal from box 41 produces Activity Counts 42 as the amplitude of the output of the sensor process reaches the appropriate level for counting. In box 43, the counts are weighted such that, in the preferred embodiment they are characterized as either high, low, or medium weight counts in a process which is explained in detail below.

In a preferred embodiment, where the sensor is used to regulate pacing rate, the output of the weighted count produces a Sensor Counts signal 44 which is used a by a rate calculation process 45 to produce a Target Rate 46. The Target Rate is than smoothed by acceleration deceleration box 47 to produce a sensor rate and the sensor rate in the preferred embodiment can be used (48) in a feedback to provide better smoothing in box 47. The sensor rate may require translation 49 to produce the pacing rate 50.

Figure 5:
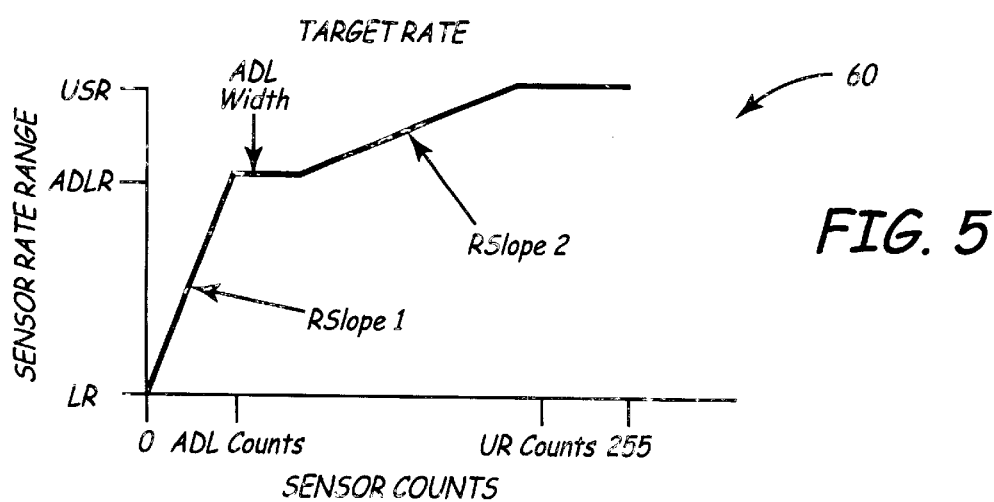
FIG. 5 is a graph of target pacing rate in accord with use of an embodiment of the invention, plotted by Sensor Counts and sensor rate.

Again, in the preferred embodiment, the production of a Target Rate from Sensor Counts occurs according to a sensor rate range curve. Referring to a preferred embodiment rate range curve 60 in FIG. 5, it is easy to see that the number of Sensor Counts can be translated into a Target Rate along the curve. It should be noted that this is just one form of preferred rate response curve and that it is not necessary to use one that has any particular configuration nor any number of separately sloped portions. It should also be noted that in preferred embodiments, the sloped portions are variable and settable by a physician or other support personnel to be most appropriate for a particular patient. The curve illustrated here is composed of two rate slopes (RSlope 1 and RSlope 2) and has flat periods at the activities of daily living rate (ADLR) and the Upper Sensor Rate (USR) thus at zero counts, the Target Rate of the sensor rate range is at the lower rate (LR) at zero counts. When the number of counts reaches the number of counts specified by the ADL counts (i.e. at the ADLRate), then, for the activities of daily living (ADL) width, the Target Rate remains the same. Going from a lower rate to the ADL rate is a fairly steep slope to enable a patient to achieve a sufficient increase in cardiac output on the initiation of exercise. During more strenuous exercise RSlope 2 rates take effect until the upper sensor rate (UR) is reached at which time the Target Rate remains constant. As mentioned earlier, these curves and also, the levels of ADL and UR are settable by medical personnel.

Figure 10:
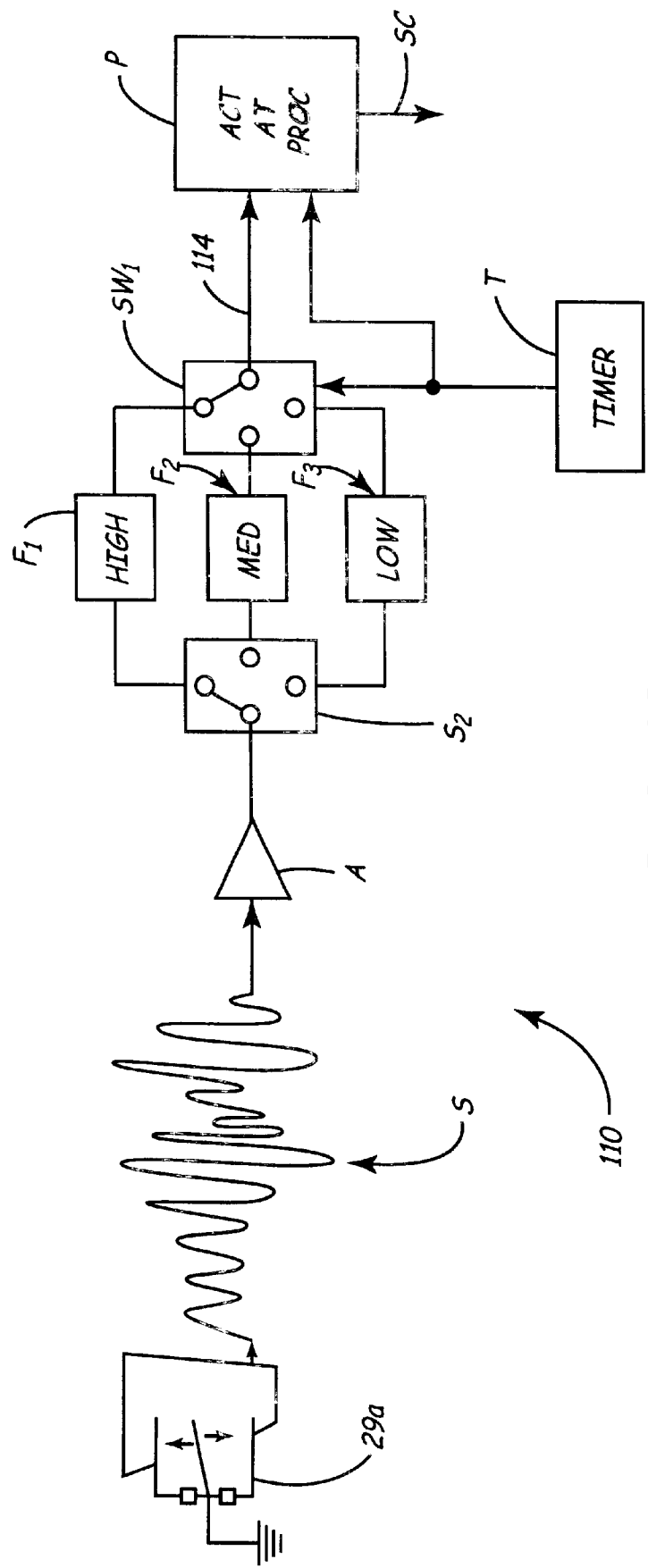
FIG. 10 is a heuristic block diagram illustrating the conversion of accelerometer signal into Sensor Counts in accord with an embodiment of the invention.

Refer now to FIG. 10 for heuristic representation 110 of the translation of accelerometer sensing signals S into Sensor Counts SC. In accelerometer sensor 29a, in one preferred embodiment is capacitive in nature, and thus the movement of the proof mass produces a time varying amplitude capacitance signal S. Preferably this will be amplified by amplifier A and the output sent to three threshold-like circuits F1, F2, F3, timed, in a preferred embodiment separately by a switch circuit S2, correspondingly timing the output with switch circuit SW1. These threshold circuits or T circuits may in fact be counters, flip-flops, or other retriggerable or triggerable devices, which produce a signal output (preferably) each time the value of the amplitude of the amplified signal S achieves a certain level (like a threshold) above a baseline (or below it). They may count zero crossings or produce counts based on having the amplitude be over a given predetermined level for a set period of time, or may work according to any of the numerous and generally well known methods of producing a numeric and preferably integer or digital representation of amplitude change or absolute level of an amplitude varying signal over time. In the heuristic model 110, a switch SW1 is activated by a timer to vary between connecting the high medium and low thresholds output to the activity count processor P. It will be appreciated by those of ordinary skill in the art that there are numerous circuits which could produce similar results to the heuristic model described in FIG. 10. It is essential merely that there be multiple levels of counts produced from the output of the accelerometer and that each level of these counts be evaluated independently based on the amplitude of the signal S reaching one of the at least three levels. In the activity count processing block P, in enhancement is made to the values produced by the higher level signals. In other words, if threshold circuit F3 were to produce four counts over a period (in the preferred embodiment a two second period) those four counts may pass directly out of the sensor count line SC as the sensor count signal. If however (again in this example) the threshold circuit F2 would produce the same count (4) the activity count processor would enhance that by some fact, in the preferred embodiment 2 thus the output SC would produce a count of 8. In the same example, in one preferred embodiment the enhancement for the output from threshold circuit F1 that, for example, produced a count of 4 on line 111 the output SC would then be 16. Thus, the activity count processor for process P produces a higher sensor count for the same amount of Activity Counts coming from threshold circuit F1 than it does from threshold circuit F2 and even more than threshold circuit F3. Thus the dynamic range in the potential sensor count change is wider with this invention than with the prior art since the total is from three circuits for counting crossings in a unit of time rather than from one, and because at least two of them have a multiplier applied to their output. Note that in the most preferred embodiment, we employ the outputs in a round robin or serial manner, having first threshold circuit F1, then threshold circuit F2, then threshold circuit F3 report output for a two second period onto line 111. There is inherently no reason we could not simply accumulate the output from all three threshold circuits F1–F3 to produce the same wide range of values after a shorter period of time for a given activity level or acceleration. However in the currently preferred embodiment the activity count process (or processor) P produces a Sensor Count signal reflective of all three threshold circuits F1–F3 weighted output every 6 seconds, by producing one output count every two seconds, from the three circuits in order. There is also no reason why we could not use more than three threshold circuits if such an added complexity were found to be advantageous, however three seems most preferred at this time.

Although all the circuits that could be used are within the ordinary skill of the engineer in this field, we believe that by describing in more detail the potential circuits for arranging to count level crossings in the amplitude varying accelerometer signal, the reader will more easily understand the usefulness of the invention.

Figure 11:
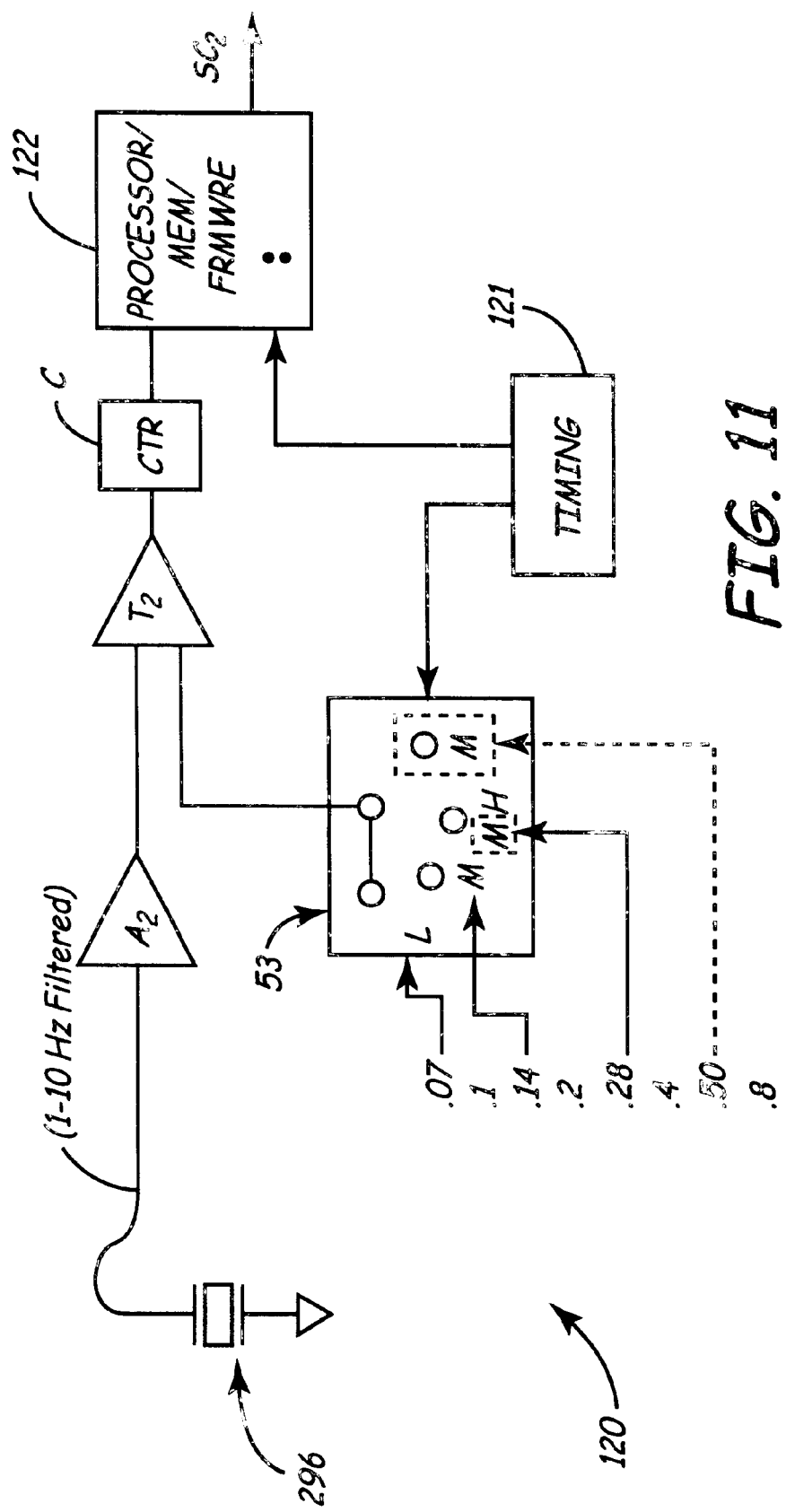
FIG. 11 is a block diagram of a current implementation of a preferred form of the embodiment accelerometer signal to activity count circuit.

Typically a bandpass filter is used to isolate the appropriate frequency of acceleration signal change before the first amplifier illustrated in the circuits of FIGS. 10 and 11, typically in a range of 1–10 Hz.

In the currently most preferred embodiment we trade off the flexibility of having three separate threshold circuits for the power saving simplicity of using a single such circuit and measuring at three levels in a temporal series. For a description of this please refer to FIG. 11, in which a model 120 having an accelerometer sensing circuit 29b feeding an amplitude varying signal into an amplifier A2. When the output of the amplifier A2 matches the level selected in block S3, the thresholding circuit F2 produces a count for the counter circuit C, which in turn counts out to the processor and memory circuit running under program control, which in turn produces the weighted count output SC. Just as in the circuit in FIG. 10, a timing circuit 121 provides coordinating signals for the processor circuitry 122 and the switching circuitry S3. The main difference here is instead of separately programmable thresholding circuits; a single thresholding circuit is programmed to three settings and switched between them at two-second intervals. The settings themselves are programmable just as they were in FIG. 10, but only one level settable switch S3 is needed in this design. (Note that by dotted line here we illustrate that 3 or 4 settings are preferred in the switch block S3).

The activity count process of using weightings for the output counts from three circuits which count amplitude crossings at different levels can, after this disclosure, easily be implemented in software or hardware by those of ordinary skill in this art, in many different forms besides the one diagramed here.

Figure 3:
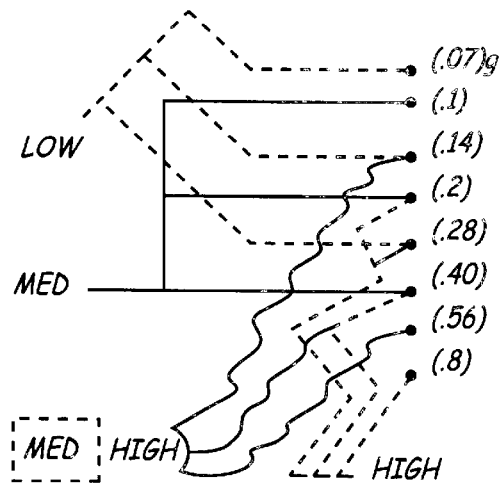
FIG. 3 is a diagram of acceleration of gravity values corresponding to high, medium and low settings of thresholding or threshold circuits in accord with one aspect of an embodiment of the invention.

Refer now to FIG. 3, in which a series of values is (identified) in as gs or acceleration level due to gravity which could be of any range chosen to match activity levels of bodies into which such devices are to be implanted, the orientation of the accelerometer, or other factors that a designer could consider. We chose values ranging from 0.07 to 0.8 and assume the direction of acceleration/deceleration to be in or out of the plane of the hybrid circuit board. In one preferred embodiment, the accelerometer had been employed will have been tested such that the output of the signal at a set voltage level will match the output of the three threshold circuits as values approximately those indicated here. However, others may use similar values if desired, and may have only one setting for the plurality of sensor signal height monitoring threshold circuits (F1–F3). It is another feature of this invention to enable a low, medium and high range for a plurality of thresholds or threshold crossing detection's circuits described with reference to FIGS. 10 and 11, in whatever form they take. Thus, at 0.07 gs, the low threshold circuit F3 would respond when the signal S crosses that value. The medium threshold circuit F2 would respond at a signal level of 0.14 gs and the high threshold circuit F1 would respond a 0.28 gs. when the threshold circuit(s) F1–F3 were set into the low setting. At the medium setting, 0.1 gs, 0.2 gs, and 0.4 gs provide the threshold levels at which these threshold circuits would respond by producing an activity count when the signal S crosses those levels. In the high setting 0.14 gs, 0.8 gs, and 0.56 gs would correspond to the levels of the threshold circuits F1, F2, F3. (FIG. 3 also has a fourth setting, which could be used above the high level, and if so, we would call the high level "medium high" or med hi, and the highest level (the forth level) just "high" or hi. In some embodiments we use just three settings and in some we use four, both of which are indicated on this FIG. 3. Of course, the numbers can be varied by one of ordinary skill in this art if desired, and the g-figures are for illustrative purposes only, even though they represent the settings for our currently preferred embodiments.

In the currently most preferred embodiment we use four threshold levels, which would be four threshold circuits for the embodiment of FIG. 10 or four settings for the threshold circuit of FIG. 11. In particular we use the following settings: 0.07, 0.14, and 0.28 for the lo, med, and hi settings for the threshold circuit(s); 0.1, 0.2, 0.4 for the mid range sensitivity threshold circuit(s); and we use a medium hi and hi threshold, where the medium hi setting for the three threshold levels is 0.14, 0.28, and 0.56 gs; and finally, the hi settings for the threshold circuit(s) would be at 0.2, 0.4 and 0.8 gs for the three threshold settings for the threshold circuit(s).

Refer now to FIG. 2 and FIG. 4 together. (FIG. 4 assumes a constant setting for the threshold circuits F1–F3, or a single set of three (or four) levels being employed serially by a single threshold circuit S3). The sensor counts of each type (from the high, medium, and low threshold circuits) are illustrated in the graph of FIG. 4, measured along the x-axis and timed along the y-axis. In the prior art, only a single threshold level was available which would produce an output of Sensor Counts similar to the lines indicated by the medium count MC, low count LC, or high count HC lines in this graph. Note that by combining them with a multiplication factor, the weighted counts WC curve is much higher as the medium and high count numbers increase even slightly (see WC incr vs. HC incr on the graph for example). Thus, it is believed that at the initiation of strenuous exercise the patient can achieve the higher rate pacing or the upper sensor pacing rate very quickly relative to the capacity achievable by prior art responses. In the prior art where only a single range or threshold is used for the determination of sensor counts, the same rapid response to change is unavailable.

Figure 7:
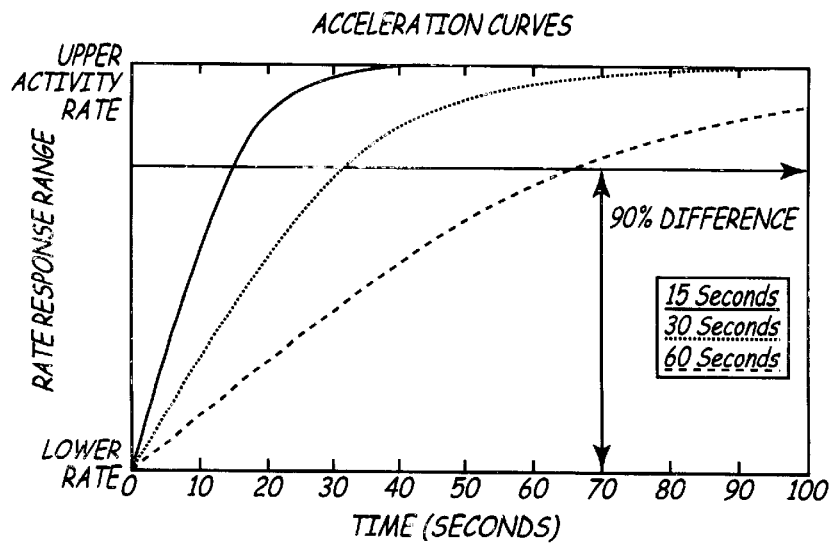
FIG. 7 is an acceleration curve for use with an embodiment of the invention.
Figure 8:
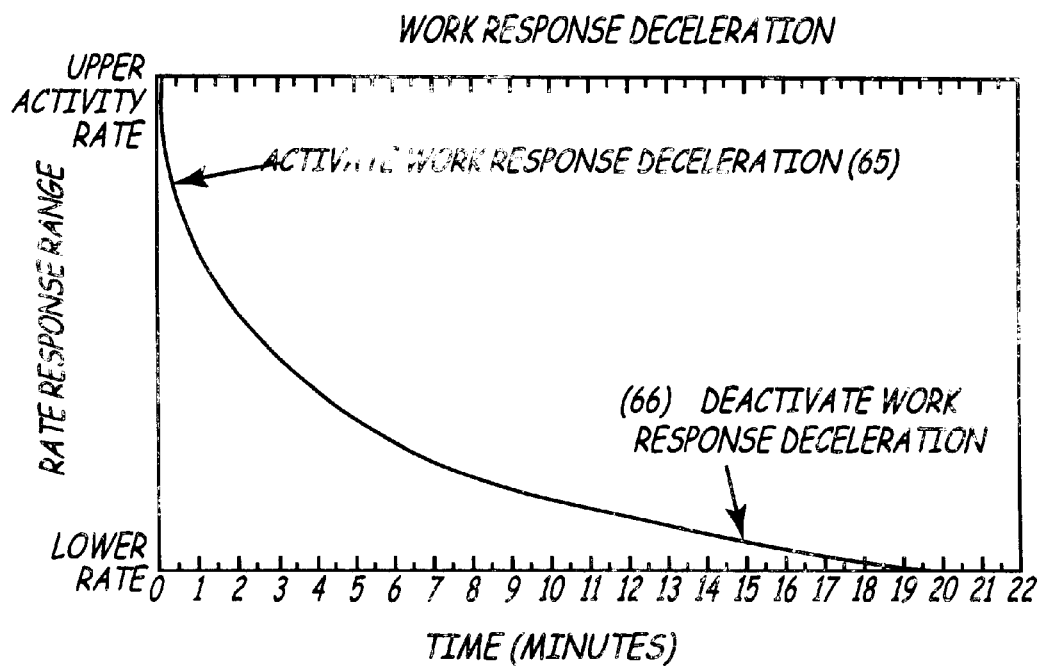
FIGS. 8 and 9 are deceleration curves for use with an embodiment of the invention.
Figure 9:
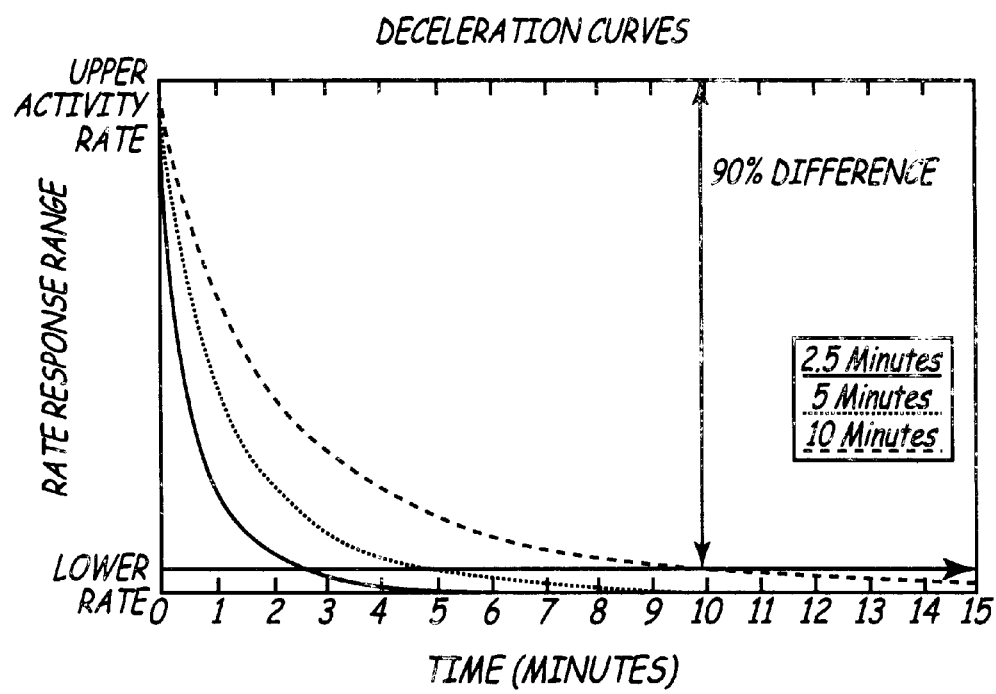

It is believed necessary or at least helpful to also provide some smoothing of the transition between a pacing rate currently employed and one which might be suggest to be changed by a target rate a very short period of time later. Accordingly, in a system where the sensor rate is translated directly into the pacing rate (as indicated in FIG. 2), the sensor rate is fed back into to process 47 by which the acceleration or deceleration curves are applied to the target rate changes. FIGS. 7, 8, and 9 illustrate how these curves are applied. (Such curves can also be applied to a multi-sensor system as illustrated at block 108 in FIG. 6, discussed later).

Referring to FIG. 7 it can be seen that over a time of 100 seconds there are three acceleration curves, which can apply to the rate response change. At the maximum rate of change, 90% change can occur in about 15 seconds, while at the lowest acceleration curve, 70 seconds is required to make the change. Because of the wider response level available with the weighted plurality of sensor outputs for a given activity change profile, the number of counts can be matched to the curves more easily. A range of over 30 counts may be available with this invention whereas a range of less than ten counts per short time interval will be available in prior art rate response algorithms. Having a selectable set of acceleration curves gives the medical worker an opportunity to match the paced heart's response to the change in acceleration in accord with a patient's age and capacity, and thus the three curves are provided in preferred embodiment pacemaker implementations of this invention.

When a patient activity level decreases, it may be even more important to match the pacing rate deceleration to the needs and capacity of the patient. Accordingly, in FIG. 8, a period of rapid change in acceleration or ultimately the Target Rate gets a short period of time and small rate drop before the deceleration response process limits the deceleration of the pacing rate in accordance with a selected deceleration curve from FIG. 9.

Figure 6:
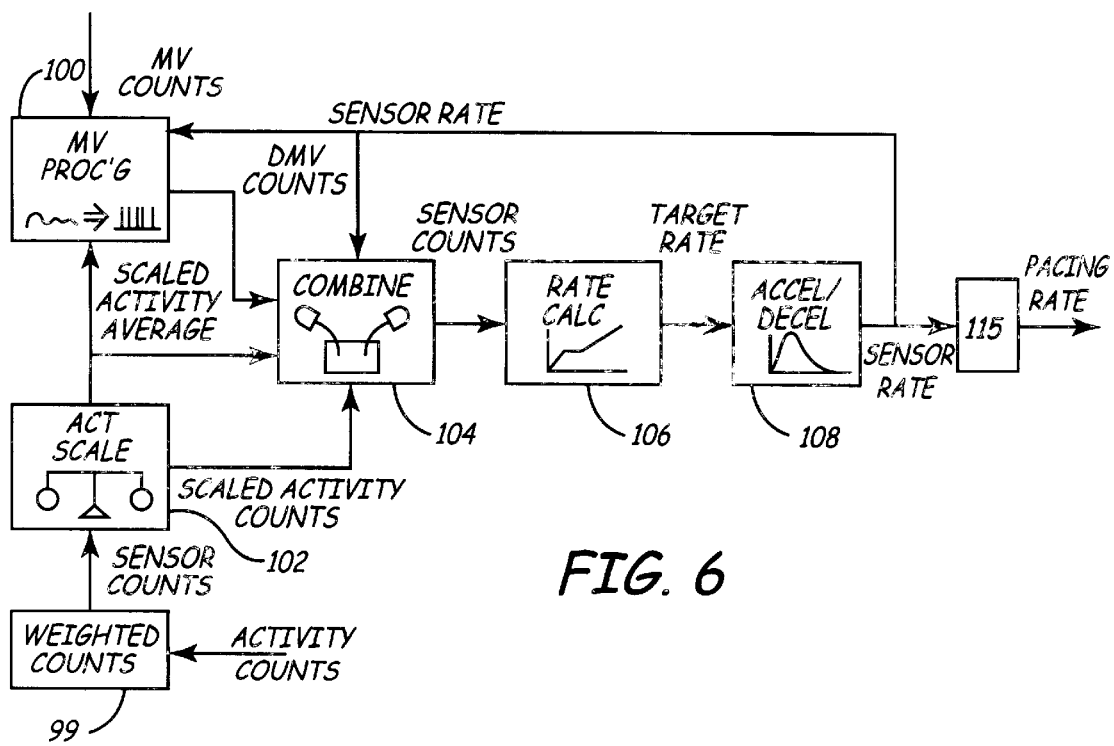
FIG. 6 is a block diagram illustrating application of the invention in a multi sensor environment for producing a single pacing rate signal.

These acceleration and deceleration limits to changes in the pacing rate are applied at block 47 in FIG. 2 and block 108 of FIG. 6.

Referring now to FIG. 6, the same blocks used to produce Sensor Counts from FIG. 2 (41, 42, 43, 44, here block 99) can be employed to produce the Sensor Counts feeding into the scaling block 102 of FIG. 6. FIG. 6 illustrates how the Activity Counts which are weighted as described earlier in this embodiment of this invention, can be employed with additional sensors to produce a pacing rate. In this preferred embodiment, there are Minute Ventilation counts (MV COUNTS), which are similar to activity counts, but likely to be reported by the circuitry on a different scale. For a detailed explanation of how this process of scaling and MV Count production works, the reader is referred to the prior art Yerich patent cited previously and incorporated hereinto by reference. The Yerich patent also provides a detailed description of the other elements of this block diagram, to demonstrate how the counts from the activity sensor (a piezoelectric crystal in that patent rather than an accelerometer as used here) are combined after scaling, how the Target Rate is calculated and how the acceleration and deceleration curves applied to produce a Sensor Rate (or as described in Yerich, a Sensor Interval). Similarly to the functioning of the circuitry of the block diagram of FIG. 2 at line 49, there will need to be a conversion of the Sensor Rate to a Pacing Rate, here in FIG. 6 accomplished by conversion circuitry block 115.

It should also be noted that within the circuitry as defined for a preferred embodiment and which should be available for any preferred device employing this invention would be a memory circuit for storing data produced by this invention. Thus, the counts produced by any or all of the threshold circuits, or the Sensor Counts, or the Target Rate or the Sensor Rate or the Pacing Rate should be storable in a histogram form if desired for analysis and relation to other physiologic data on a patient.

The telemetry capable devices of FIG. 1 can either upload a segment of memory storing such data or telemeter it out at such time as it is generated, if desired to a device similar to device 19. The programmer-type device 19 can of course either make a display or printout of either the raw data, or some process enhanced description or illustration of it, or transfer such data across a communications network to physicians or other medical workers or automatic systems which may then employ the data for diagnostic, therapeutic, or research purposes.

The inventors believe the foregoing to describe the invention fully to one of ordinary skill in the art to which it pertains, and that the invention can be produced from such description without undue experimentation, and believe the scope of the invention to be limited only by the following appended claims.

What is claimed is:

1. An activity count producing circuit determining activity count values in an (Implantable Medical Device) IMD, comprising:

means for receiving amplitude and frequency varying output signal from an accelerometer in the IMD, a plurality of threshold circuits receiving the accelerometer output signal, each threshold circuit of the plurality of threshold circuits having a corresponding plurality of threshold levels and producing sensor count outputs corresponding to amplitude components of the accelerometer output signal that exceed a corresponding threshold level of the plurality of threshold levels for each of the plurality of threshold circuits to produce a count of a number of times each of the corresponding threshold levels are exceeded, and, combining circuit means for combining the sensor count outputs from said plurality of threshold circuits.

2. An activity count producing circuit as set forth in claim 1 further comprising means for weighting the sensor count outputs, and summing the zero crossings or time periods over the plurality of thresholds to produce an activity count signal.

3. An activity count producing circuit as set forth in claim 1, wherein a first threshold level corresponding to a first threshold circuit of the plurality of threshold circuits is approximately equal to a first signal level in a first setting and a second signal level, not equal to the first setting, in a second setting, and a second threshold level corresponding to a second threshold circuit of the plurality of threshold circuits is approximately equal to a third signal level in the first setting and a fourth signal level, not equal to the third signal level, in the second setting.

4. A rate-responsive implantable medical device having an accelerometer sensor responsive to patient activity to produce a sensor output signal indicative of the level of patient activity, comprising:

a plurality of threshold circuits, each threshold circuit having a different threshold level and producing activity count signals in response to the sensor output signal being greater than the threshold level of the threshold circuit, each threshold circuit having an input to receive the sensor output signal and an output providing the activity count signals;

a first switch sequentially coupling the sensor output signal to the input of each of the threshold circuits;

an activity count processor producing a sensor count signal as a function of the activity count signals produced by the threshold circuits;

a second switch sequentially coupling the output of each threshold circuit to the activity count processor; and means for controlling the first and second switches to couple each threshold circuit to the accelerometer sensor and to the activity count processor for a predetermined dwell time.

5. An implantable medical device for implantation within a user and having an accelerometer for producing a sensing output signal representing activity levels of the user, comprising:

a plurality of threshold circuits receiving the sensing output signal, each threshold circuit of the plurality of threshold circuits having a corresponding variable threshold level and producing activity counts in response to the sensing output being greater than the corresponding variable threshold level;

a combiner circuit combining the activity counts from said plurality of threshold circuits and producing sensor counts; and wherein a first threshold level corresponding to a first threshold circuit of the plurality of threshold circuits is approximately equal to a first signal level in a first setting and a second signal level, not equal to the first signal level, in a second setting, and a second threshold level corresponding to a second threshold circuit of the plurality of threshold circuits is approximately equal to a third signal level in the first setting and a fourth signal level, not equal to the third signal level, in the second setting.

6. A method for producing a measure of activity from an accelerometer comprising:

sampling an accelerometer output signal for a short first period of time in a first circuit of a set of accelerometer monitoring and count producing circuits;

producing a count representing a level of activity sensed by said first circuit using a threshold level corresponding to the first circuit;

sampling an accelerometer output signal for a short next through last of a set of periods of time in a next through last set of circuits of said set of accelerometer monitoring and count producing circuits;

producing counts representing a level of activity sensed by said next through last set of circuits using threshold levels corresponding to the next through last set of circuits;

weighting said counts at a predetermined weight unique to each of said set of circuits; and producing a weighted sensor count output from each count produced by each of said set of circuits, wherein the threshold levels utilized in the steps of producing counts corresponds to respective first signal levels for the first circuit and the next through last set of circuits in a first setting, and respective second signal levels, not equal to the first signal levels, for the first circuit and the next through last set of circuits in a second setting.

7. The method of claim 6 wherein said step of producing a weighted sensor count output from each count produced by each of said set of said circuits is produced seriatim.

8. A method for generating sensor counts representing activity levels of a user of an implantable medical device, comprising the steps of:

generating sensing outputs corresponding to activity levels of the user;

generating, in response to the sensing outputs, a first count using a first threshold level and a second count using a second threshold level; and combining the first count and the second count and outputting corresponding sensors counts, wherein the first threshold level is approximately equal to a first signal level in a first setting and a second signal level not equal to the first signal level in a second setting, and the second threshold level is approximately equal to a third signal level in the first setting and a fourth signal level, not equal to the third signal level, in the second setting.

* * * * *